(12) United States Patent
Karitonas

(10) Patent No.: US 11,701,444 B2
(45) Date of Patent: Jul. 18, 2023

(54) METHOD AND APPARATUS FOR DISINFECTION

(71) Applicant: SPECIALIST HEALTH SOLUTIONS LIMITED, Norfolk (GB)

(72) Inventor: Tautvydas Karitonas, Hampton Vale (GB)

(73) Assignee: SPECIALIST HEALTH SOLUTIONS LIMITED, Norfolk (GB)

( * ) Notice: Subject to any disclaimer, the term of this patent is extended or adjusted under 35 U.S.C. 154(b) by 470 days.

(21) Appl. No.: 17/023,810

(22) Filed: Sep. 17, 2020

(65) Prior Publication Data

US 2021/0060198 A1 Mar. 4, 2021

Related U.S. Application Data

(60) Division of application No. 16/252,850, filed on Jan. 21, 2019, now Pat. No. 10,780,190, which is a
(Continued)

(30) Foreign Application Priority Data

Feb. 27, 2012 (AU) .............................. 2012100211
Feb. 29, 2012 (GB) .................................... 1203542

(51) Int. Cl.
*A61L 2/22* (2006.01)
*A61L 2/24* (2006.01)
(Continued)

(52) U.S. Cl.
CPC ................. *A61L 2/22* (2013.01); *A61L 2/186* (2013.01); *A61L 2/24* (2013.01); *B05B 12/02* (2013.01);
(Continued)

(58) Field of Classification Search
None
See application file for complete search history.

(56) References Cited

U.S. PATENT DOCUMENTS 5,492,273 A 2/1996 Shah
2004/0050951 A1 3/2004 Mmero
(Continued)

FOREIGN PATENT DOCUMENTS

WO 2004062800 A1 7/2007
WO 2009138430 A1 11/2009
WO 2011047127 A1 4/2011

*Primary Examiner* — Holly Kipouros
(74) *Attorney, Agent, or Firm* — Tarolli, Sundheim, Covell & Tummino L.L.P.

(57) ABSTRACT

A process and apparatus for disinfection of spaces using a disinfecting liquid droplet spray atomization are described, in which an electric fan 107 is used to dispense the atomization from an atomization chamber 104 via venture outlets 106 into the space to be disinfected. The operation of the electric fan 107 is modulated in a cycle having a first phase in which the fan is operated at full speed and a second phase at which the fan is operated at a randomly selected speed to vary the rate of dispensing into the space in order to improve the dispersal of the atomized droplets in the space and hence the efficacy of disinfection.

9 Claims, 6 Drawing Sheets

Figure 1:
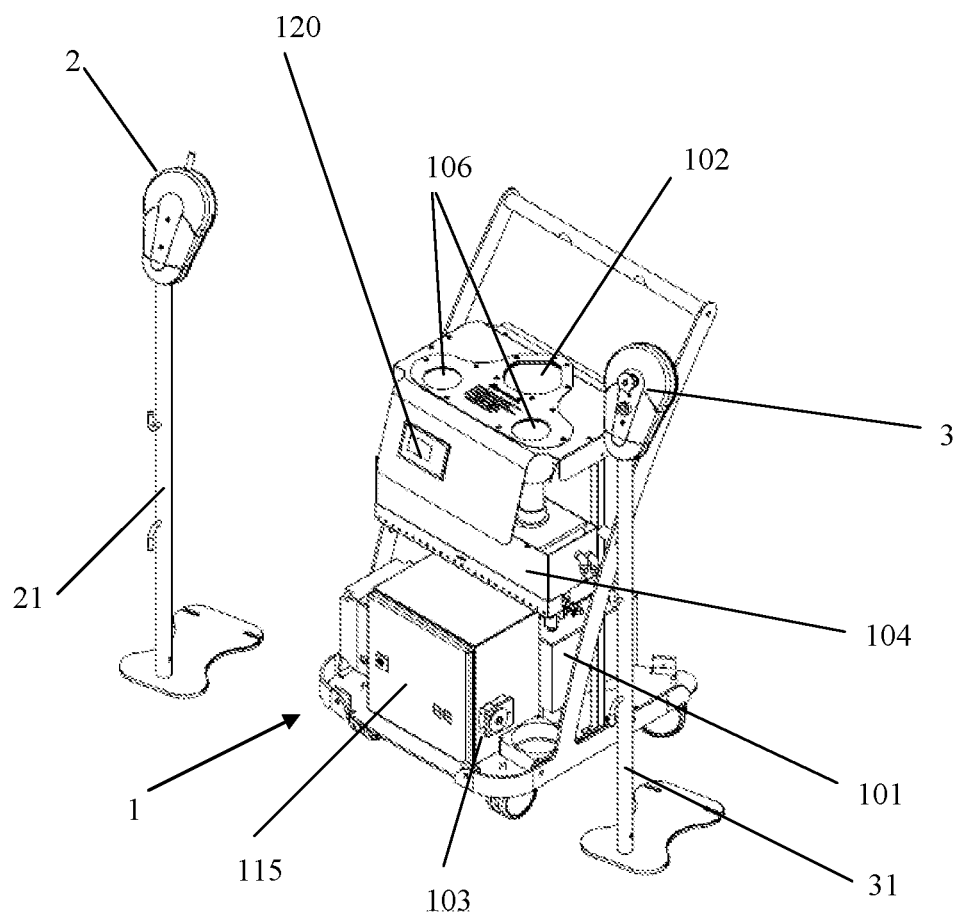
Figure 2:
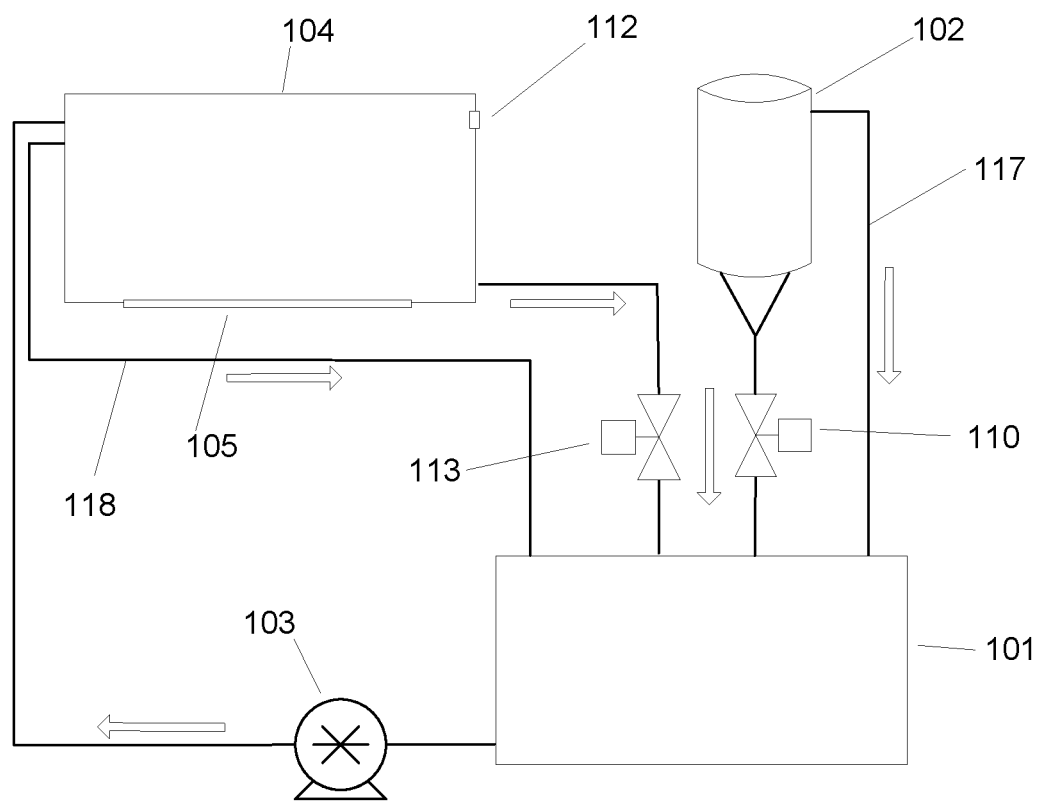
Figure 3:
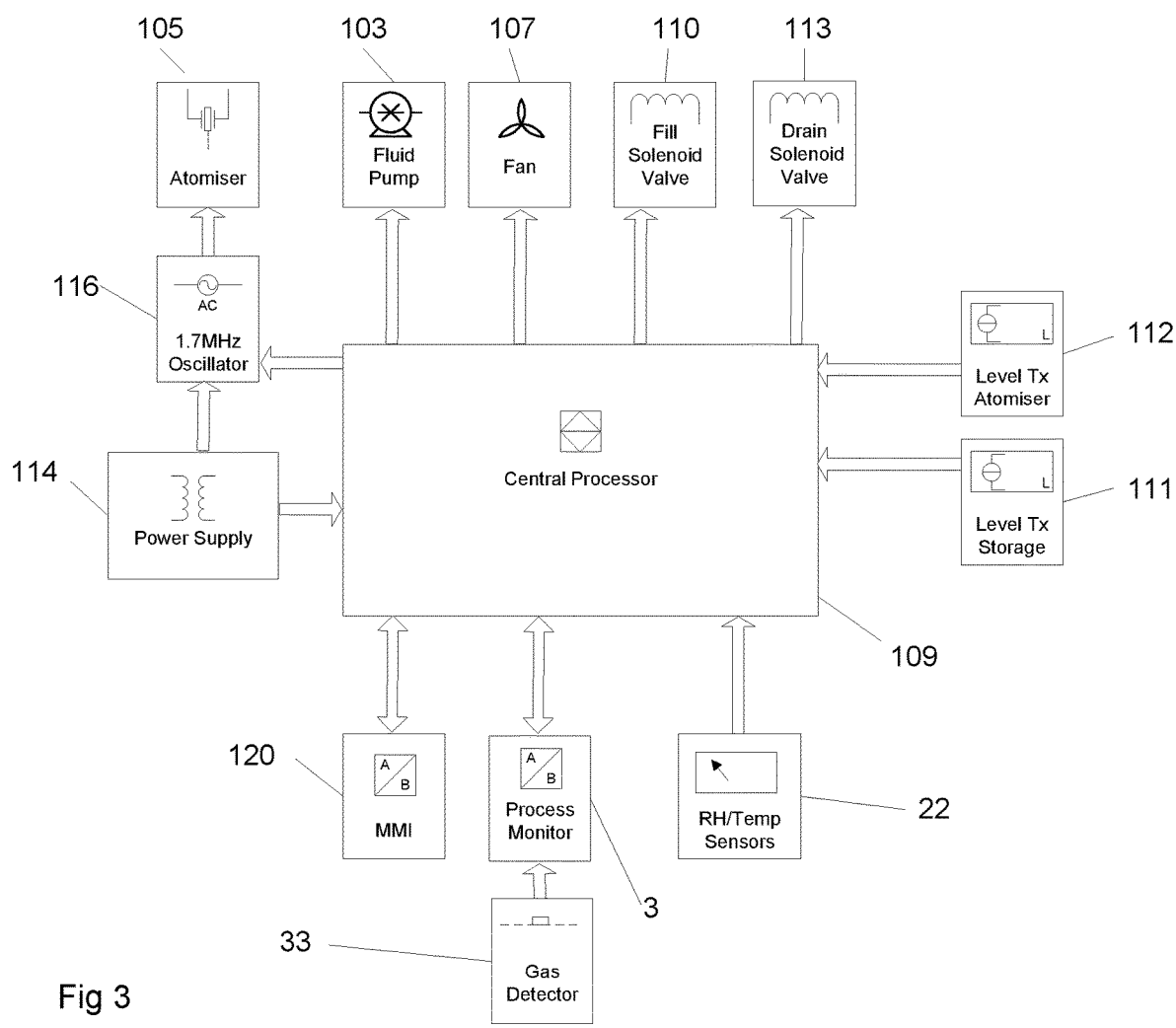
Figure 4:
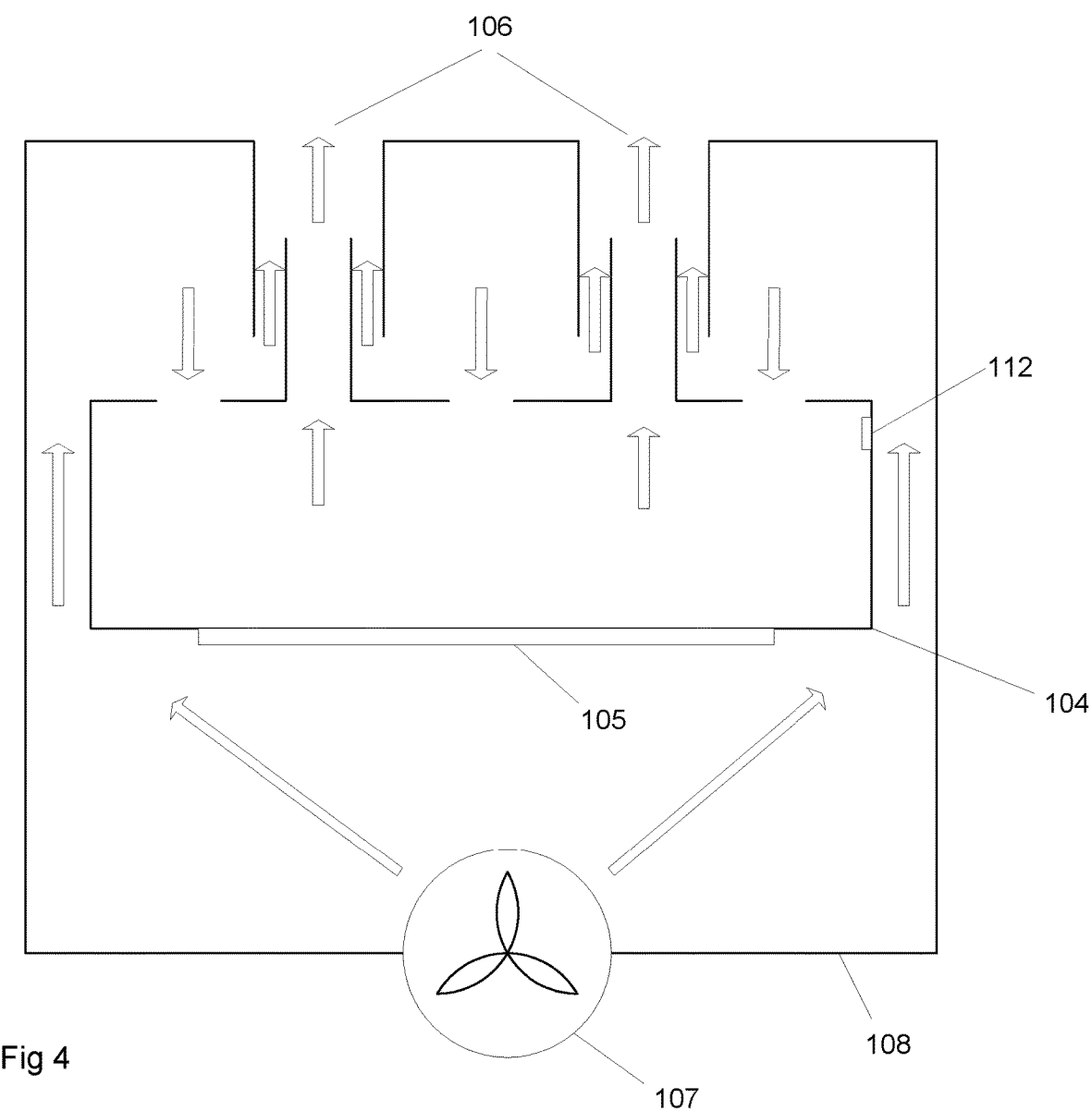

Related U.S. Application Data continuation-in-part of application No. 14/381,334, filed as application No. PCT/GB2013/050477 on Feb. 27, 2013, now Pat. No. 10,195,302.

(51) Int. Cl.
  *A61L 2/18* (2006.01)
  *B05B 12/02* (2006.01)
  *B05B 17/06* (2006.01)

(52) U.S. Cl.
  CPC ........ *A61L 2202/11* (2013.01); *A61L 2202/14* (2013.01); *A61L 2202/15* (2013.01); *A61L 2202/16* (2013.01); *A61L 2202/25* (2013.01); *B05B 17/06* (2013.01)

(56) References Cited

U.S. PATENT DOCUMENTS

| | | |
|---|---|---|
| 2005/0224596 A1 | 10/2005 | Panopoulos |
| 2008/0038166 A1 | 2/2008 | Hill |
| 2008/0292498 A1* | 11/2008 | Resch ................ C01B 13/10 422/107 |
| 2011/0114744 A1 | 5/2011 | Ricciardi et al. |

* cited by examiner

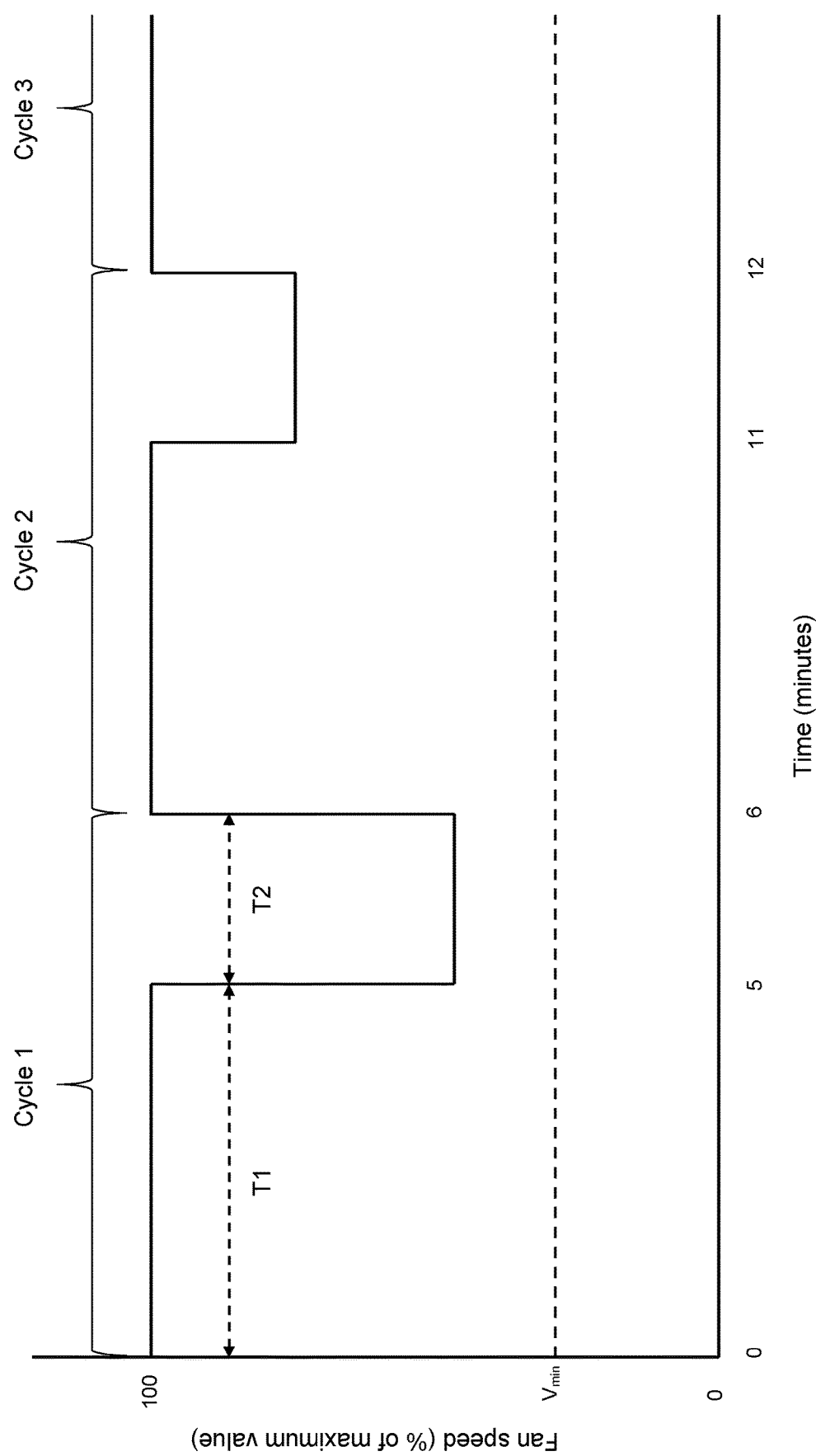

METHOD AND APPARATUS FOR DISINFECTION

This application is a Divisional of U.S. patent application Ser. No. 16/252,850, filed 21 Jan. 2019, which is a Continuation-in-Part of U.S. patent application Ser. No. 14/381,334, filed on 27 Aug. 2014, which is a U.S. National Stage application under 35 USC 371 of PCT Application No. PCT/GB2013/050477, filed on 27 Feb. 2013; which claims priority from AU 2012100211, filed 27 Feb. 2012, and GB 1203542.4, filed 29 Feb. 2012, the entirety of all of which are incorporated herein by reference.

BACKGROUND

The present invention relates to a method and apparatus for disinfecting spaces such hospital rooms and the like.

The problem of micro-organism contamination of, for example, hospital bedrooms and the like has grown into an acute one in recent years and one particular method of disinfecting such spaces and any equipment located therein is the use of disinfecting sprays (atomisations) of liquid droplets such as hydrogen peroxide. These systems are often known as hydrogen peroxide fogging systems and such hydrogen peroxide fogging systems can involve vaporization of a low concentration hydrogen peroxide solution using a high frequency ultrasound (typically 1.6-2 MHz) droplet generator in an atomization chamber partially filled with solution. WO-A-2009-138430 discloses such a system and method designed to provide improved efficacy of such methods and which involves the steps of: (a) determining a first value of the relative humidity of the air in the space; (b) atomizing a disinfecting liquid in the space until a predetermined second value of the relative humidity of the air is reached in the space, and; (c) maintaining the relative humidity of the air for a predetermined time at the second value by means of atomizing the disinfecting liquid, wherein the method further comprises of decreasing the relative humidity of the air in the space prior to and/or during atomizing of the disinfecting liquid.

In such processes, under the influence of the ultrasonic droplet generator and through the mechanism of forced cavitation, small sized droplets (circa 1 µm diameter) are produced and ejected from the solution surface. Airflow from an electric fan then carries these droplets as a mist from the chamber via a venturi into the space to be treated. A combination of the fan's airflow and natural convection currents in the room carry these droplets until they contact surfaces where they are deposited and operate to destroy any organisms present. Given appropriate generating capacity for the space to be disinfected, if sufficient vaporised hydrogen peroxide is expelled from the system, statistically a good fog density and hence hydrogen peroxide distribution will be achieved in the space.

This traditional process is controlled via a closed loop system, with relative humidity (RH) being the controlling variable as described in WO-A-2009-138430. Tests have shown that in a closed environment (which is required for safety), RH increase is proportional to hydrogen peroxide concentration increase.

One of the primary factors affecting efficacy of the process is the profile of the airflow within the space being treated. Traditionally, with a regular electric fan operating in a closed space with no external ventilation (as required for safety), a reasonably static air distribution pattern is achieved which, depending on the layout of the room and its contents, can lead to areas of poor fogging coverage and hence droplet deposition, a phenomenon known as spatial differentiation and this in turn can lead to incomplete disinfection.

SUMMARY OF THE INVENTION

According to the present invention, a process for disinfection of spaces using a disinfecting liquid droplet spray (atomisation), in which a fan is used to dispense the atomisation into the space to be disinfected, can be improved by modulating the operation of the electric fan in a substantially random sequence.

Apparatus for carrying out the method comprises a hydrogen peroxide fogging device having an electric fan for dispensing a fog of hydrogen peroxide droplets into a space to be disinfected, and a control system for modulating the operation of the electric fan in a substantially random sequence.

Preferably, apparatus for carrying out the process includes a venturi injector into which atomized droplets are introduced as a secondary airflow and the electric fan is arranged to provide a primary flow of entraining air through the venturi into which the atomized droplets are entrained for dispensing into the space to be disinfected.

This can be achieved by controlling the 'duty cycle', i.e. the ON/OFF cycle of operation of the fan in accordance with a pseudo-random sequence. This may have the effect of adjusting the fan speed, depending on the time periods being used. Alternatively, the fan speed may be varied directly by adjusting the electrical power supplied to it in accordance with a desired pseudo random characteristic. A particularly effective pseudo-random sequence has been identified and is described below and in connection with FIG. 6.

The following disclosure defines an injection phase in which disinfecting liquid is injected into the air within a space to be disinfected. During this phase, the relative humidity of the air increases. This is because the disinfecting liquid is provided in a solution containing water, such that introduction of the disinfecting liquid into the air correspondingly introduces water into the air as well. Thus, it will be appreciated that the relative humidity is a proxy for measuring the concentration of disinfecting liquid in the air of the space being disinfected.

The injection phase has an associated injection time, which is the time that the apparatus remains operating in the injection phase. The relative humidity at the start of the injection phase is referred to as the initial relative humidity.

The following disclosure also defines a dwell phase, in which the relative humidity in the space has reached a target relative humidity. The dwell phase has an associated dwell time, which is the time that the apparatus remains operating in the dwell phase.

The combination of the target relative humidity and dwell phase duration are selected such that together they result in effective disinfecting of the space. Effective disinfection may be defined as a target reduction in the number of microorganisms on a surface within the space, e.g. a 'log 5' or 'log 6' reduction. A lower target relative humidity may have a correspondingly longer dwell phase duration to achieve the same efficacy as a higher relative humidity.

Preferably, during the injection phase the apparatus is configured to calculate a rate of change of the relative humidity of the air in the space. The rate may be determined using data gathered by one or more sensors of the apparatus over a predetermined time period. Based on the calculated rate, the apparatus calculates whether the target relative humidity is expected to be achieved at or before the end of the injection phase.

In the event that the apparatus calculates that the target relative humidity will be achieved at or before the end of the injection phase, the target relative humidity remains the same and the apparatus selects a dwell time based on the fact that the target relative humidity is expected to be achieved within the injection phase. The apparatus also continues injecting disinfecting liquid for the duration of the injection phase.

In the event that the apparatus calculates that the target relative humidity will not be achieved at or before the end of the injection phase, the apparatus checks whether the difference between the current relative humidity and the initial relative humidity is above a threshold value. If the difference is greater than or equal to the threshold value, the apparatus terminates the injection phase and moves into the dwell phase. The apparatus also selects a dwell time based on the fact that the target relative humidity was not expected to be achieved within the injection phase.

If the difference is less than the threshold, the apparatus remains in the injecting phase and continues injecting the disinfecting liquid into the air in the space. The apparatus checks again at one or more later times whether the measured relative humidity is greater than or equal to the threshold and, if so, terminates the injection phase and moves into the dwell phase as discussed above.

During both the injection phase and the dwell phase, the fan is operated in a two-phase mode of operation. In a first phase the fan is operated at full speed and in the second phase the fan is operated at a randomly selected reduced speed. Here, 'full speed' refers to a maximum operating speed of the fan, which may be defined as any of: the maximum speed at which the fan is rated to operate; the maximum speed at which the fan is capable of operation; or a user-selected maximum operating speed that differs from both of the former. The maximum operating speed of the fan may have a corresponding maximum duty cycle or have a corresponding maximum electrical power being supplied to the fan, depending on the mode of control of the fan.

The speed of the fan is adjusted as follows. For the duration of a first time period, the fan is operated at full speed. At the end of this first time period, the operating speed of the fan is set at a random value between a minimum viable speed and the fan maximum speed. Preferably, the random value is greater than or equal to the minimum viable speed and less than the fan maximum speed.

The fan is operated at this randomly selected speed for the duration of a second time period. At the end of the second time period, the fan is once again operated at full speed, again for the duration of the first time period. The cycle is then repeated, with it being understood that the operating speed during each occurrence of the second time period is randomly selected and hence this operating speed in general varies from cycle to cycle.

Here, minimum viable speed is understood to mean a fan speed that is less than the maximum fan speed but at least equal to a minimum fan speed, below which dispersal of the disinfecting liquid is considered to be insufficient to enable effective disinfecting of the space. The minimum fan operating speed will depend on the specifics of the situation at hand, e.g. fan parameters such as blade dimensions and blade profile, the size of the space being disinfected, the size of the droplets of disinfecting liquid, etc., and will thus be determinable on a case by case basis by one of ordinary skill in the art having the benefit of the present disclosure.

The duration of the first and second time period can be varied from cycle to cycle, or the duration of each time period may remain the same from cycle to cycle.

The random adjustments to the fan speed have been found to promote an even and thorough distribution of disinfecting liquid throughout the entirety of the space being disinfected. Without being bound by theory, it is thought that this is because a fan operating at a constant speed establishes an air flow pattern over some characteristic timescale, which air flow pattern then does not change over time after the characteristic timescale has passed, thereby preventing optimal distribution of the disinfecting liquid within the space. Setting the fan speed at random disrupts the air flow pattern, creating turbulence in the air and promoting distribution of the disinfecting liquid throughout the space.

Preferably, the duration of the first time period is selected such that it is less than or approximately equal to the characteristic timescale over which the static air flow pattern is established. This will vary according to the specifics of a given situation, such as the dimensions of the space being disinfected, the size and shape of the blades of the fan or fans, etc. Thus, the duration of the first time period may also be selected according to the specifics of a given situation. A 'rule of thumb' type estimate may be used in place of more detailed calculations of the characteristic timescale, as it is not critical that the characteristic timescale is calculated to a high level of accuracy.

It is also not critical that the first time period is selected to be precisely less than or equal to the characteristic timescale, and the first time period may be selected to be longer than the characteristic timescale by some significant margin, e.g. 5%, 10%, 15%, 20%, etc. of the total duration of the characteristic timescale.

Again without being bound by theory, it is thought that a given fan speed has an associated characteristic timescale over which the static air flow pattern is established. The duration of the second time period may therefore be selected in dependence on the randomly selected speed for that duration, where again the second time period is preferably less than or approximately equal to the characteristic timescale associated with the randomly selected fan speed.

Preferably, the second time period is shorter than the first time period.

Optionally, the apparatus may be configured to determine a suitable duration for the first time period based upon the randomly selected fan speed of the immediately preceding cycle. The apparatus may therefore calculate a suitable duration for the first time period of each cycle on the fly, whilst the apparatus is in use. The microcontroller may be configured to perform these calculations.

During the injection phase and dwell phase, the microcontroller controls the fan speed as described above to create the required the turbulent airflow.

The random sequence may, as in the current embodiment, be provided by a software pseudo random number generator running on the control system hardware. This is used to switch the electric fan on and off using a pulse-width modulation scheme determined by the pseudo random number generator, the pulse width being determined at, or in advance of, the start of each instance of the second time period by the random number generator.

Separately from the aforementioned control cycle, it has also been discovered that using a pulse width modulation scheme with a relatively short (say 1-3 second) period for both 'ON' and 'OFF' parts of the cycle, causes the fan's speed-up and speed-down ramps to overlap, which gives rise to variable air speed.

This higher fog density in conjunction with optimisation by the control system of the attained humidity level to match the ambient temperature of the space, gives rise to micro-condensation on surfaces in the space being treated. This has been shown to increase efficacy of the decontamination process. The described maximum operating speed following by a randomly-selected fan operating speed that is greater than or equal to the minimum viable speed may create an airflow profile within the space being disinfected that is particularly effective in distributing the airborne droplets of disinfecting liquid throughout the space, increasing the probability that micro-condensation forms on substantially all surfaces within the space. This may result in an improvement of the efficacy of the disinfecting process.

While pulse width modulation is preferred, other methods of controlling the operating speed of the fan to achieve the randomized airflow profile may be used.

Randomization of the airflow has the effect of improving dissipation by introducing a more dynamic airflow, which greatly reduces the number of poor coverage areas by creating a more turbulent and random airflow within the space. Also, the atomization droplet density being expelled from the machine can be constantly changed (whilst maintaining the sub 1 μm droplet size required for mobility). This may further assist with creating a dynamic, turbulent airflow.

Preferably, additionally, the attained RH is based upon the air temperature of the space being treated, and the desired RH target is linked to the ambient temperature of the space being treated.

Once the dwell phase is complete, the apparatus enters a deactivation phase. In this deactivation phase it is required to allow a period of time for deactivation of the disinfecting liquid where it breaks down into harmless components. For example, in the case where the disinfecting liquid is hydrogen peroxide, in the deactivation phase the hydrogen peroxide breaks down into water and oxygen. During this time, the fan is controlled to operate at normal, i.e. full, single speed, operation, to maximise airflow and to minimise deactivation time.

Optionally the apparatus comprises a deactivation fan that is configured to draw air into the apparatus. The deactivation fan can be a different fan from the fan that controls injection of the disinfecting liquid into the space, or it can be the same fan. In the case where the same fan is used for injection and deactivation, preferably the fan is driven in the reverse direction in the deactivation phase so as to draw air into the apparatus rather than push air away from the apparatus.

If a second fan is present, preferably both the fan and deactivation fan co-operate in the deactivation phase, with the deactivation fan drawing air from the space into a deactivation module of the apparatus and the fan expelling processed air from the deactivation module.

The deactivation module preferably contains a catalyst that promotes the breakdown of the disinfecting liquid into harmless components.

The combination of fan modulation and venturi, gives the advantage that with a constant atomisation/fog generation rate, during the low fan speed/pwm off periods a higher fog density builds in the venturi, and is expelled as the fan speed re-increases. Given the random nature of the fan speed, the fog density is constantly changing, which also assists with generation of a turbulent airflow profile.

BRIEF DESCRIPTION OF THE ACCOMPANYING FIGURES

FIG. 1 is a perspective view of apparatus according to the invention, from the front;

FIG. 2 is a block diagram illustrating flow of hydrogen peroxide within the apparatus and the corresponding components;

FIG. 3 is a block diagram illustrating the main components of the atomisation, delivery and control components of the apparatus;

FIG. 4 is diagrammatic view illustrating the arrangement of the atomization unit of the apparatus;

FIG. 5 is a flowchart of the disinfecting process; and

FIG. 6 is a chart showing a preferred fan operating cycle during an injection phase and a dwell phase.

DETAILED DESCRIPTION

One example of apparatus according to the invention will now be described with reference to the accompanying figures described above. In the following, the disinfecting liquid is hydrogen peroxide, but the invention is not limited in this respect and other disinfecting liquids can be used instead.

The apparatus has a portable fogging unit 1 mounted on a trolley 10, and a portable relative humidity and temperature sensor unit 2 on a stand 21 or an integrated relatively humidity and temperature sensor unit provided within the housing of the apparatus. The apparatus also includes a remote control and indication unit (or process monitor) 3, likewise on a stand 31. Preferably, remote control and indication unit 3 is configured to communicate wirelessly with the apparatus and is further configured to be detachably mountable to the housing of the apparatus. Remote control and indication unit 3 preferably includes one or more of: a human interface device such as a touch-sensitive screen, preferably an LCD touch-sensitive screen; one or more handles to enable the process monitor to be easily detached from the housing and carried by an operator; an identification module configured to enable an operator to identify themselves to, and optionally authenticate themselves with, the apparatus, preferably using a wireless-enabled smart card; and a support stand pivotably coupled to the main body of the process monitor to enable the process monitor to be stood up easily and robustly by an operator.

In use, the portable fogging unit 1 and the humidity sensor unit 2 are disposed within a space to be disinfected and the remote control and indication unit 3 is disposed outside the space which is sealed from the surrounding area for safety. The remote control and indication unit is preferably in wireless communication with the portable fogging unit 1. The control and indication unit 3 includes a hydrogen peroxide monitor 33 arranged, on detecting hydrogen peroxide gas outside of the space under treatment, to provide a signal to the fogging unit 1 to halt operation of the apparatus.

The fogging unit 1 includes a storage reservoir 101 for liquid hydrogen peroxide and which is supplied from a hydrogen peroxide cartridge 102. A pump 103 is provided to supply hydrogen peroxide from the storage reservoir to an atomization chamber 104, in the base of which is provided an ultrasonic atomization unit 105. This operates in use, to generate high frequency ultrasound (typically at 1.6-2 MHz) to cause cavitation in the liquid hydrogen peroxide in the atomization chamber and hence creates a fog of atomized droplets above the level of the liquid in the atomization chamber. To create a hydrogen peroxide 'fog' within the space to be disinfected, a pair of venturi injection outlets 106 are provided, the primary (or entraining) airflow through which is provided by a fan 107 disposed within a housing 108 surrounding the atomization chamber 104. Atomized droplets entrained in the primary airflow are emitted into the atmosphere in the space to be disinfected and, in use, alight on surfaces within the space, causing those surfaces to be disinfected. The atomized droplets preferably have a diameter of around 1 µm. Overflow lines 117, 118 from the cartridge 102 and atomization chamber 104 respectively back into the storage reservoir 101 are provided to prevent overflow/spillage in case of control system failure.

The fogging unit carries a power supply 114 housed in a casing 115 and supplying power for driving the various electrical components including an oscillator 116 which in turn drives the atomization unit 105. The fogging unit 1 also includes a user interface in the form of a control panel and display 120 which provides instructions and information on the status of the operation to the operator during the setup and post-decontamination phases. It also displays error and warning messages. As it is not accessible during the process (being inside the space under decontamination), information is provided via a data cable (not shown) to the process monitor 3 which thus gives status information to the operator from outside the space during the disinfection process. Alternatively, in the case where the process monitor 3 is in wireless communication with the fogging unit 1, the data cable can be omitted.

Having now described the main components, the operation of the apparatus will now be described.

Before the treatment begins, the space to be treated is prepared by sealing doors, ventilation openings etc. and by placing the portable fogging unit 1 and the relative humidity and temperature sensor unit 2 in the space, the relative humidity and temperature sensor unit being located remote from the fogging unit 1. The process monitor 3 (remote control and indication unit) is placed outside the space to be treated.

At the start of the process a control switch (not shown) on the fogging unit 1 is operated and, via a signal to a microcontroller 109 which in turn activates a control valve 110, hydrogen peroxide liquid is admitted to the storage reservoir 101 from the supply cartridge 102. The control valve 110 allows the liquid hydrogen peroxide to enter the reservoir 101, with an electronic level sensor 111 transmitting a signal reporting reservoir level to the microcontroller 109. Multiple supply cartridges may be used before the desired level is reached in the storage reservoir 101 and the control valve 110 is closed once sufficient cartridges have been drained into the system to fill the storage reservoir.

Once the reservoir 101 is filled to the desired level as determined by the sensor 111, the control system microcontroller 109 commands the pump 103 to fill the atomization chamber 104 to a predetermined level (in this example 53-57 mm). The level in the atomization chamber 104 is communicated to the control system microcontroller 109 via a level sensor 112. Once the correct level is attained, the pump 103 is stopped and the system enters the standby state. Personnel are removed from the space and it is finally sealed.

Preferably either during or after the aforementioned process a system status check is performed to determine that all components of the fogging unit 1 are functioning within normal operating parameters. For example, a filling rate of reservoir 101 may be monitoring and compared with a nominal value. If the filling rate is found to be significantly less than the nominal value, an error indicative of a leak may be generated and displayed by the process monitor 3. Preferably, no disinfecting liquid is emitted into the air by fogging unit 1 unless the system status check reports nominal operation, to avoid the situation where disinfecting liquid is released into the air by a fogging unit that is not functioning within normal operating parameters.

Assuming the system status check indicates all systems are operational, if performed, the decontamination cycle is then started by a key operated switch on the process monitor 3. Indicators on the process monitor show the current status of the system during use. The decontamination cycle starts by reading the initial relative humidity value of the space from sensor in the RH and temperature sensor unit 2 which includes a transmitter 22 connected to the microcontroller 109, and by operating the atomization unit 105 in the atomization chamber 104. At the same time the duty cycle of the fan 107 may be pseudo-randomly varied by pulse width modulating the electrical supply to the fan. A preferred fan speed operating cycle is shown in FIG. 6.

Fog generated in the atomization chamber 104 is expelled into the space under treatment by the action of the fan 107 and venturi outlets 106.

The optimum relative humidity is the dew point of the disinfecting liquid. In the case of hydrogen peroxide, a target relative humidity of 97% is currently preferred, but it is contemplated that alternative values can instead be used. The aim is to achieve a relative humidity that approaches the dew point of water from below, but does not exceed the dew point of water. A relative humidity of 97% is thus selected as it provides a suitable margin for error in a relative humidity feedback control system that uses a humidity sensor to determine the current relative humidity and adjust disinfecting liquid output accordingly. It is contemplated that future improvements, e.g. improved humidity sensor technology, may enable a higher relative humidity to be targeted in future, e.g. 98%, 99%, 99.5%, etc., and such embodiments are thus within the scope of the invention.

Initially, the target relative humidity is set to the target value, e.g. 97%. During the injection phase, the microcontroller is configured to determine a rate of change of the relative humidity based on data gathered over a predetermined time period that in this embodiment is the immediately preceding five minutes. Values other than five minutes may alternatively be used.

The microcontroller uses the calculated rate of change to determine whether the target relative humidity will be reached in the remaining time of the injection phase, which in this embodiment lasts for 60 minutes in total unless it is ended early per the following disclosure.

If the microcontroller calculates that the relative humidity will reach the target relative humidity before the end of the injection phase, the fogging unit 1 continues to generate hydrogen peroxide vapor until the end of the injection phase such that, at the end of the injection phase, the relative humidity is at the target relative humidity. In this case, the dwell phase duration is set as 30 minutes.

If the system calculates that the relative humidity will not reach the target relative humidity before the end of the injection phase, the system determines whether the relative humidity has increased by at least 20% compared with the initial relative humidity. If this increase is found, then the fogging unit 1 is switched to the dwell phase before the end of the injection phase and the dwell phase duration is set as 60 minutes. If the increase in relatively humidity is less than 20%, the system continues to generate hydrogen peroxide vapor and repeats the above-discussed calculation after a further five minutes has passed to see if the change in relative humidity is at that point greater than 20%.

Figure 5:
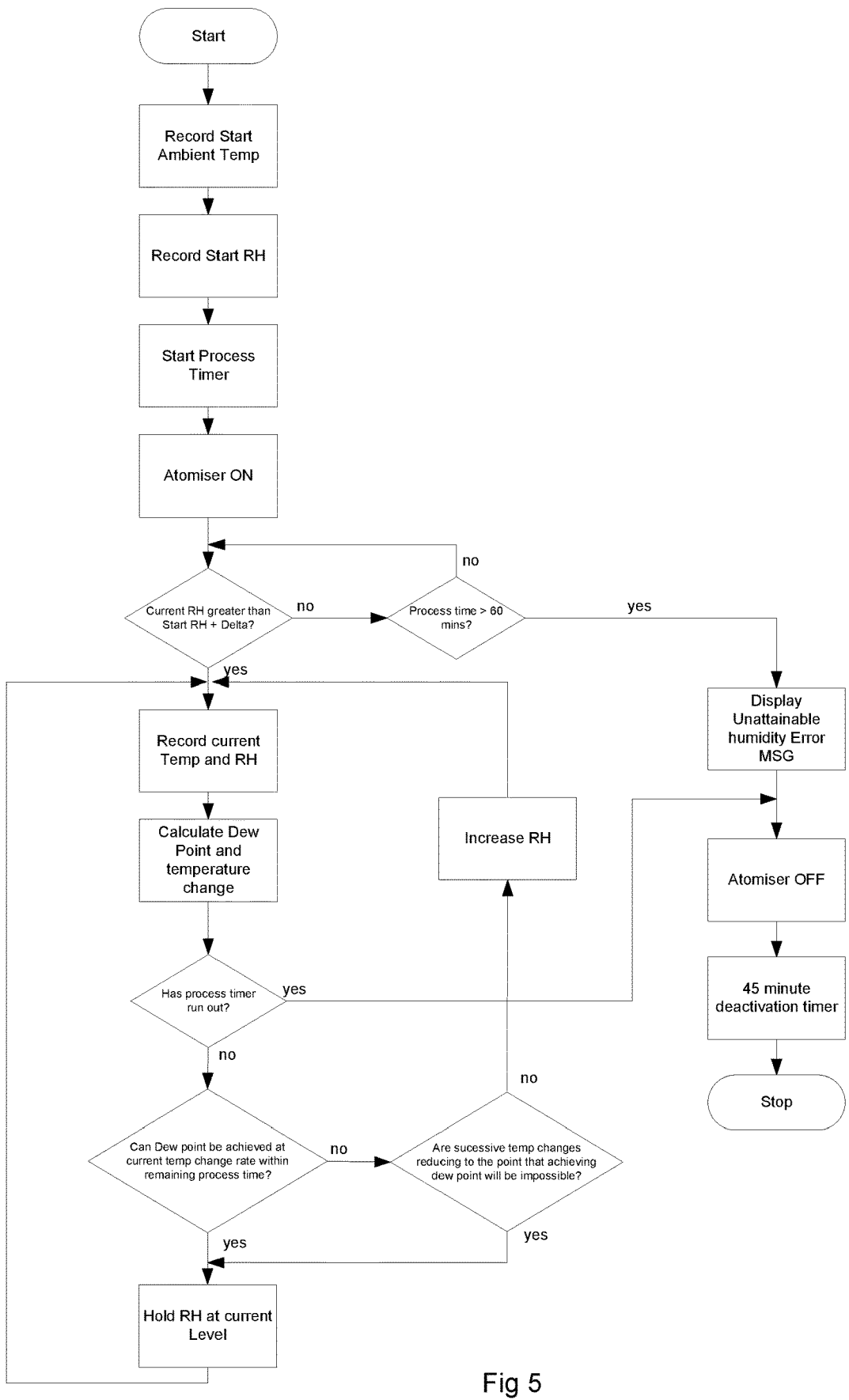

The fogging unit may determine an optimum relative humidity that is different from the initial target relative humidity based on current temperature measured from RH sensor unit and other programmable parameters as described below in relation to the flowchart of FIG. 5. When this RH level is attained, the atomization unit 105 in the atomization chamber 104 is controlled in a closed loop system including the microcontroller 109 to hold this level accurately for the duration of the dwell phase of the process, which dwell phase duration is selected in dependence on whether the optimum relative humidity was calculated to be within the 60 minute duration of the injection phase. The atomization unit preferably includes multiple transducers disposed over the bottom of the atomization chamber, but all driven by the same input signal. The fluid level in the atomization chamber 104 is also held at 53-57 mm by a closed loop control system between the pump 103, level sensor 112 and the central processor 109.

During the injection and/or dwell phase, the control system microcontroller preferably also logs the ambient temperature. Once the desired RH level is reached and rather than just holding this RH level static, changes in ambient temperature can be monitored to change the setpoint of the atomization RH control system. The process is illustrated in the flowchart of FIG. 5 which is self-explanatory.

Since heating and ventilation to the space under treatment is blocked/disabled during a disinfection process, the temperature generally falls over the course of a disinfection cycle. This can be improved by heating the space prior to decontamination, and removing the source of heat just prior to starting decontamination. In practice, the dew point may be approximated by: $T_{dew}=T_{ambient}-(100-RH/5)$, which, although not dimensionally correct, has been found, as a rule of thumb approximation to be generally accurate to within a degree or so, as long as the RH is over 50% (which it is at the point in the process where the approximation is used). This is sufficiently accurate to fulfil the requirements of the control system. It is desirable to achieve micro-condensation on surfaces where possible to improve efficacy (this occurs significantly at the dew point), the control system microcontroller 109 monitors the rate of change of ambient temperature via the RH and temperature sensor unit 2, and attempts to attain an RH value which gives rise to the dew point being achieved during the process as the temperature falls. For example, if the RH (after the initial period of increase) is 70%, the change in temperature over a 5 minute period has been −0.5° C., the current ambient temperature is 20° C., and there is 45 minutes of process time remaining, the dew point will be approximately 14 degrees. With a temp loss of 0.1° C./minute one would need 60 minutes to reach the dew point, but only 45 minutes remain. The control system calculates the required RH to achieve the dew point within the remaining time at the current rate of change of temperature. In this case, the temperature would drop by only 4.5 degrees (assuming a fixed rate of change), so the RH would need to be increased to 77.5% to achieve dew point during the process. Of course, rate of change of temperature during the process is not constant and will reduce as thermal equilibrium is approached. The control system is adaptive and constantly changing based upon the above relationship. It may not be possible to achieve dew point for every disinfection operation (if there is little or no ambient temperature change during the process), and in this case, the control system switches to the operational mode described above in which it holds a ceiling RH that it as least 20% greater than the initial RH.

When the dwell phase is completed, the deactivation phase begins. In the deactivation phase the atomization unit 105 is turned off, and the fan modulation ceases, with the fan 107 then being driven at maximum speed to provide a full 120 $m^3$/hr for a further deactivation period (45 minutes in the current example), while the hydrogen peroxide breaks down. Whilst this deactivation period is current, the control system microcontroller 109 instructs control valve 113 to open, draining any remaining fluid from the atomization chamber 104 back into the storage reservoir 101 for subsequent re-use.

A deactivation fan (not shown) that remains powered off during the earlier phases is turned on in the deactivation phase. The deactivation fan draws air into the deactivation module (not shown) of the apparatus, to promote air flow through the apparatus. Fan 107 is also driven, to expel air that has passed through the deactivation module away from the apparatus. In this manner, rapid deactivation of the air in the space can be achieved.

The deactivation module includes a chamber containing a carbon filter and one or more carbon pallets. Preferably, activated carbon is used. The one or more carbon pallets and carbon filter are structured to maximize their surface area, such that air entering the deactivation module encounters a relatively large surface of activated carbon. This large surface area means that the rate of deactivation is high, reducing the overall time required for the deactivation phase.

After this deactivation period, signals on the process monitor 3 indicate to the operator that it is safe to return to the space. During the set up and post process phases, the control panel and display 120 provides instructions to the operator, and also displays and warning/error messages.

In a particular example, tests have shown a random fan operating time between 1 and 3 seconds to be suitable, with pauses of similar length (also randomly determined by the pulse width modulator). This range allowing a 750 ml volume (chamber capacity above liquid level) to be fog filled between fan cycles, gives an increased fog density as compared to running the atomizer with a fan running permanently at the full 120 $m^3$/hr rate.

FIG. 6 shows a preferred fan operating control cycle for use during the disinfecting phase of the process. Each cycle shown in FIG. 6 has two portions; a first time period T1 and a second time period T2.

During first time period T1, the fan is operated at maximum speed. Preferably, the first time period T1 is less than or approximately equal to the characteristic time over which an air flow pattern is established in the space at the maximum fan operating speed. Five minutes for the first time period T1 has been found to be suitable for the size of space in which the apparatus described herein is typically used. However, deviations from this value are of course possible.

At the end of first time period T1, the fan operating speed is set at a random value that is greater than or equal to the minimum viable fan operating speed $V_{min}$ and less than the maximum fan operating speed. In a particular embodiment, $V_{min}$ is 40% of the maximum fan operating speed. A suitable value for $V_{min}$ will be identified by one of ordinary skill in the art according to the specifics of a given implementation.

The random value can be generated by a pseudo-random number generator. The fan is operated at the randomly selected operating speed for the second time period T2. Preferably, second time period T2 is shorter than first time period T1. The duration of the second time period T2 may be selected based on a characteristic time is less than or approximately equal to the characteristic time over which an air flow pattern is established in the space at the random fan operating speed.

One minute for the second time period T1 has been found to be suitable for the size of space in which the apparatus described herein is typically used. However, deviations from this value are of course possible.

At the end of second time period T2, the first cycle is complete. The fan operating speed returns to maximum, and the second cycle begins. This cyclic mode of operation is repeated until the disinfecting phase is complete.

The fan operating speed in the second time period T2 is randomly selected and therefore in general varies from cycle to cycle.

The duration of the first time period T1 may vary from cycle to cycle, or it may be the same for each cycle. The duration of the first time period T1 may be set based upon the randomly selected operating speed of the fan in the second phase of the immediately preceding cycle.

The duration of the second time period T2 may vary from cycle to cycle, or it may be the same for each cycle.

It will be appreciated that FIG. 6 shows an idealized operation in which fan speed is adjustable instantaneously. In a practical implementation it of course takes some small but non-zero time to adjust the fan speed. The time for adjustment of the fan speed will be small compared to the duration of the first time period T1 and the second time period T2 such that the adjustment time can be ignored in a practical implementation.

Additional embodiments which may form the subject of this application or any continuation or continuation in part applications filed subsequent to this application are set out below.

Embodiment 1: A process for disinfection of spaces using a disinfecting liquid droplet spray atomization, in which an electric fan is used to dispense the atomization into the space to be disinfected, wherein the speed of the fan is controlled in accordance with a pseudo-random number generator for adjusting the speed of the fan.

Embodiment 2: A process according to Embodiment 1, in which the duty cycle of the fan is modulated in accordance with the pseudo-random number generator.

Embodiment 3: A process according to Embodiment 1, wherein the fan is operated by a pulse-width-modulated (PWM) signal the period of which is modulated in accordance with the pseudo-random number generator.

Embodiment 4: A process according to Embodiment 1, in which atomized droplets are introduced into a venturi injector and the fan creates a primary flow of entraining air through the venturi and into which the atomized droplets are entrained for dispensing into the space to be disinfected.

Embodiment 5: A process according to Embodiment 1, in which the relative humidity of the air within the space is determined prior to the fan starting.

Embodiment 6: A process according to Embodiment 1, in which status information is provided to a display outside of the space under treatment.

Embodiment 7: A process according to Embodiment 1, in which a hydrogen peroxide monitor is disposed outside of the space under treatment and is arranged so that, on detecting hydrogen peroxide gas outside of the space under treatment, the process is halted.

Embodiment 8: Apparatus, comprising a hydrogen peroxide fogging device having an electric fan for dispensing a fog of hydrogen peroxide droplets into a space to be disinfected, and a control system configured to control the speed of the fan in accordance with a pseudo-random number generator for adjusting the speed of the fan.

Embodiment 9: Apparatus according to Embodiment 8, in which the duty cycle of the fan is modulated in accordance with the pseudo-random number generator.

Embodiment 10: Apparatus according to Embodiment 8, wherein the fan is operated by a pulse-width-modulated (PWM) signal the period of which is modulated in accordance with the pseudo-random number generator.

Embodiment 11: Apparatus according to Embodiment 8, including a venturi injector into which atomized droplets are introduced as a secondary airflow and the fan is arranged to provide a primary flow of entraining air through the venturi into which the atomized droplets are entrained for dispensing into the space to be disinfected.

Embodiment 12: Apparatus according to Embodiment 8, including means for monitoring the relative humidity of the air within the space to be disinfected.

Embodiment 13: Apparatus according to Embodiment 8, including means, separate from the fogging device and which may be located outside of the space under treatment, to display status information in operation.

Embodiment 14: Apparatus according to Embodiment 8, including a hydrogen peroxide monitor locatable outside of the space under treatment and arranged, on detecting hydrogen peroxide gas outside of the space under treatment, to provide a signal halt operation of the apparatus.

Embodiment 15: A process for disinfection of spaces using a disinfecting liquid droplet spray atomization, in which an electric fan is used to dispense the atomization into the space to be disinfected, wherein the speed of the fan is controlled in a substantially random manner, in which the duty cycle of the fan is modulated in accordance with a the substantially random sequence.

Embodiment 16: Apparatus, comprising a hydrogen peroxide fogging device having an electric fan for dispensing a fog of hydrogen peroxide droplets into a space to be disinfected, and a control system configured to control the speed of the fan in a substantially random manner, in which the control system is configured to modulate the duty cycle of the fan in accordance with a the substantially random sequence.

The invention claimed is:

1. A process for disinfection of a space using a disinfecting liquid droplet spray atomization, in which an electric fan is used to dispense a fog of hydrogen peroxide droplets into the space to be disinfected, comprising:
   modulating the operation of the electric fan in a sequence, the sequence comprising a first phase having a first duration and a second phase having a second duration, wherein in the first phase the fan is operated at a maximum operating speed and in the second phase the fan is operated at a randomly selected operating speed that is greater than or equal to a minimum viable fan operating speed
   calculating a rate of change of a relative humidity of air within a space being disinfected over a predetermined time period during an injection phase in which disinfecting liquid is being injected into the air within the space;
   calculating, based on the rate of change, whether a target relative humidity will be reached at or before an end of the injection phase;
   in the affirmative, continuing the injection phase and setting a duration of a dwell phase to a first dwell phase duration; and
   in the negative, determining whether a difference between a measured relative humidity and an initial relative humidity is greater than a predefined threshold value and, in the affirmative, ending the injection phase and setting the duration of the dwell phase to a second, different, dwell phase duration;

wherein the initial relative humidity corresponds to a relative humidity measurement taken before the start of the injection phase.

2. A process according to claim 1, wherein the first duration is less than or approximately equal to a characteristic timescale over which an airflow pattern is established in the space.

3. A process according to claim 1, wherein the sequence is a first cycle, the process comprising repeating the sequence as a second cycle.

4. A process according to claim 3, including setting the first duration of the first phase of the second cycle in dependence upon the randomly selected operating speed of the second phase of the first cycle.

5. A process according to claim 1, wherein the first duration is approximately 5 minutes and the second duration is approximately 1 minute.

6. A process according to claim 1, including setting the minimum viable fan operating speed at a value below which effective distribution of a disinfecting liquid within a space to be disinfected is not achieved.

7. A process according to claim 1, wherein the predetermined time period is approximately five minutes, the predefined threshold value is approximately 20%, the first dwell phase duration is approximately 30 minutes and the second dwell phase duration is approximately 60 minutes.

8. A process according to claim 1, including introducing atomized droplets into a venturi injector as a secondary airflow and, with the fan, creating a primary flow of entraining air through the venturi and into which the atomized droplets are entrained for dispensing into the space to be disinfected.

9. A process according to claim 1, wherein the electric fan is housed in a fogging device, the process including providing a status displaying module, separate from the fogging device and which may be located outside of the space under treatment, to display status information in operation, the status displaying module configured for wireless communication with the fogging device.

* * * * *